(12) United States Patent
Asleson et al.

(10) Patent No.: US 11,766,556 B2
(45) Date of Patent: Sep. 26, 2023

(54) CANNULA FIXATION DEVICE

(71) Applicant: Medtronic, Inc., Minneapolis, MN (US)

(72) Inventors: Andrea J. Asleson, Maple Grove, MN (US); Michael P. Campbell, Blaine, MN (US); Teresa Whitman, Dayton, MN (US); Keith D. Anderson, Minneapolis, MN (US); Bridget A. Portway, White Bear Township, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 226 days.

(21) Appl. No.: 16/375,480

(22) Filed: Apr. 4, 2019

(65) Prior Publication Data
US 2020/0316275 A1 Oct. 8, 2020

(51) Int. Cl.
*A61M 60/857* (2021.01)
*A61B 17/00* (2006.01)
*A61B 17/34* (2006.01)

(52) U.S. Cl.
CPC ....... *A61M 60/857* (2021.01); *A61B 17/0057* (2013.01); *A61B 2017/00252* (2013.01); *A61B 2017/00606* (2013.01); *A61B 2017/3488* (2013.01)

(58) Field of Classification Search
CPC .............. A61M 60/857; A61M 27/002; A61B 17/0057; A61B 2017/00606; A61B 2017/00252; A61B 2017/3488; A61B 2017/00592; A61B 2017/00597; A61B 2017/3484; A61B 2017/348
See application file for complete search history.

(56) References Cited

U.S. PATENT DOCUMENTS

| 2004/0211433 A1 | 10/2004 | Albright |
| 2005/0059984 A1* | 3/2005 | Chanduszko ...... A61B 17/0401 606/151 |
| 2005/0165344 A1* | 7/2005 | Dobak, III ............ A61F 2/2476 604/8 |

(Continued)

OTHER PUBLICATIONS

PCT/US2020/019424, PCT The International Search Report and Written Opinion, dated Jun. 9, 2020, 10pages.
(Continued)

*Primary Examiner* — Richard G Louis
(74) *Attorney, Agent, or Firm* — Medler Ferro Woodouse & Mills PLLC (57) ABSTRACT

A medical fixation device which may include an elongate body with a proximal portion, a distal portion, and define a longitudinal axis extending therethrough. A first fixation member on the proximal portion of the elongate body and a second fixation member on the distal portion of the elongate body may also be included with the medical fixation device. The first fixation member and the second fixation member may each have a delivery configuration in which the first fixation member and the second fixation member are collapsed along the longitudinal axis, and an anchoring configuration in which the first fixation member and the second fixation member each extend radially outward from the elongate body, define a septal aperture therebetween, and each have a tip facing away from each other.

15 Claims, 5 Drawing Sheets

(56) References Cited

U.S. PATENT DOCUMENTS

| | | | |
|---|---|---|---|
| 2005/0273135 A1* | 12/2005 | Chanduszko | A61B 17/0057 |
| | | | 606/213 |
| 2007/0179527 A1 | 8/2007 | Eskuri et al. | |
| 2007/0225760 A1 | 9/2007 | Moszner et al. | |
| 2008/0109069 A1 | 5/2008 | Coleman et al. | |
| 2008/0249562 A1* | 10/2008 | Cahill | A61B 17/0057 |
| | | | 606/215 |
| 2009/0326572 A1 | 12/2009 | Peh et al. | |
| 2011/0270239 A1 | 11/2011 | Werneth | |
| 2011/0303229 A1* | 12/2011 | Najafi | A61M 25/01 |
| | | | 128/899 |
| 2014/0296908 A1 | 10/2014 | Ottma et al. | |
| 2015/0066077 A1 | 3/2015 | Akpinar | |
| 2017/0014113 A1* | 1/2017 | Ma | A61B 17/12122 |
| 2017/0281840 A1* | 10/2017 | Larose | A61M 60/857 |
| 2018/0110468 A1* | 4/2018 | Goldshtein | A61B 17/0057 |
| 2019/0046170 A1* | 2/2019 | Coyle | A61B 17/12122 |
| 2020/0316351 A1 | 10/2020 | Asleson et al. | |

OTHER PUBLICATIONS

Sree Karanam, Md, et al., Balloon Dilatation of the Atrial Septum to Facilitate Trans-septal Access to the Left Atrium, The Journal of Innovations in Cardiac Rhythm Management.

Mohamad Alkhouli, Md, et al., Transseptal Techniques for Emerging Structural Heart Interventions, JACC: Cardiovascular Interventions, vol. 9, No. 24, 2016.

SickKidsStaff, Balloon atrial septostomy, https://www.aboutkidshealth.ca/Article?contentid=1668&language=English.

International Preliminary Report on Patentability from International Application No. PCT/US2020/019424, dated Oct. 14, 2021 8 pp.

* cited by examiner

CANNULA FIXATION DEVICE

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to components and methods for fixating a cannula within the heart of a living subject for use with devices such as ventricular assist devices and associated elements.

BACKGROUND

Mechanical circulatory devices (MCDs) such as artificial hearts, ventricular assist devices (VADs) and other blood circulating systems and components have become more and more widely used to provide cardiovascular support to a variety of different patients. The development of these types of devices has surged in the past several decades and has led to significant medical advancements. Patients with heart conditions may survive and in some instances thrive with the use of MCDs where in the past these types of patients did not survive. The mortality and morbidity of patients is significantly reduced if MCDs are used at the appropriate time to prevent further cardiovascular issues and systemic organ failure.

Certain types of heart conditions may severely limit a patient with symptoms impacting their daily life even with minimal exertion and/or rest. Many of these patients need additional cardiovascular support and may have to be in the hospital to receive invasive medical interventions. Some have to wait for an eligible heart transplant, and the waiting time can be very long. Other patients may not be eligible for a heart transplant because of underlying medical conditions and therefore are forced to spend significant periods of time in the hospital due to ongoing heart related issues and instability.

With the invention of MCDs, these types of devices can assist the heart with pumping and circulating blood throughout the entire body. For example, this type of support can help provide blood pressure support and improve blood flow to many different organs which in turn can improve organ function. As an example, MCDs may be used as a bridge to a transplant and help a patient in heart failure survive until a donor heart is available for a transplant. In some patients waiting for a transplant, these types of devices may allow the patient to function in an outpatient setting requiring minimal medical interventions.

Additionally, these types of devices may provide long-term support for patients who are not transplant candidates. This can also allow the patient to function outside of a hospital setting with the additional cardiovascular support provided by MCDs. However, use of MCDs requires blood to be moved in the heart. There is no easy way to move oxygenated blood from the left side of the heart to a device in the right side of the heart.

SUMMARY

In accordance with the present invention, various devices, components, and methods associated with the fixation of a cannula within tissue are set forth. The present invention advantageously provides a cannula fixation device. The cannula fixation device may comprise an elongate body having a proximal portion, a distal portion, and defining a longitudinal axis extending therethrough; a first fixation member on the proximal portion of the elongate body; and a second fixation member on the distal portion of the elongate body, the first fixation member and the second fixation member each having: a delivery configuration in which the first fixation member and the second fixation member are collapsed along the longitudinal axis; and an anchoring configuration in which the first fixation member and the second fixation member: each extend radially outward from the elongate body; define a septal aperture therebetween; and each have a tip facing away from each other.

In one aspect of the embodiment, the elongate body defines a channel sized to receive a cannula therein.

In one aspect of the embodiment, the first fixation member and the second fixation member extend transversely with respect to the elongate body in the anchoring configuration and the tip defines a distal most end thereof.

In one aspect of the embodiment, the cannula has a proximal end and a distal end and at least one from the group consisting of the first fixation member and the second fixation member is disposed three to five millimeters from the distal end of the cannula.

In one aspect of the embodiment, the septal aperture is between one to three millimeters in length.

In one aspect of the embodiment, the first fixation member and the second fixation member are made of a mesh material.

In one aspect of the embodiment, the mesh material is flexible.

In one aspect of the embodiment, the mesh material includes a plurality of wires having a diameter between 0.004-0.008 inches (0.01016-0.02032 centimeters).

In one aspect of the embodiment, the first fixation member and the second fixation member each have an interior surface facing each other in a parallel orientation.

In another embodiment, the medical fixation device, comprises: an elongate body having a proximal portion, a distal portion, and defining a longitudinal axis extending therethrough, the elongate body sized to receive a cannula therein; a first fixation member on the proximal portion of the elongate body; and a second fixation member being diametrically opposed to the first fixation member on the distal portion of the elongate body, the first fixation member and the second fixation member defining a septal aperture therebetween and each: extending in a radial direction from and surrounding the elongate body when coupled with a septum disposed within the septal aperture; and having a thickness tapering in the radial direction.

In one aspect of the embodiment, the first fixation member and the second fixation member have a delivery configuration in which the first fixation member and the second fixation member are collapsed along the longitudinal axis.

In one aspect of the embodiment, the first fixation member and the second fixation member have an anchoring configuration in which the first fixation member and the second fixation member define a septal aperture therebetween.

In one aspect of the embodiment, the first fixation member and the second fixation member are made of a mesh material.

In one aspect of the embodiment, the mesh material includes a plurality of wires between 0.004-0.008 inches (0.01016-0.02032 centimeters) in diameter.

In one aspect of the embodiment, the mesh material is braided.

In one aspect of the embodiment, the plurality of wires include between 36 to 72 wires.

In one aspect of the embodiment, the distance between the first fixation member and the second fixation member is between one and three millimeters.

In one aspect of the embodiment, the cannula has a proximal end and a distal end, the distal end of the cannula is releasably secured to the elongate body.

In one aspect of the embodiment, the cannula terminates in a beveled tip.

In another embodiment, the medical fixation device may comprise: an elongate body having a proximal portion, a distal portion, and defining a longitudinal axis extending therethrough, the elongate body sized to receive a cannula therein, the cannula defining a proximal end, a distal end and including a tip at the distal end; a first fixation member on the proximal portion of the elongate body; and a second fixation member being diametrically opposed to the first fixation member on the distal portion of the elongate body, the second fixation member being disposed at least three to five millimeters proximal to the tip at the distal end of the cannula, the first fixation member and the second fixation member defining a septal aperture therebetween and being disposed a distance between one to three millimeters from each other, the first fixation member and the second fixation member each: extending in a radial direction from and surrounding the elongate body when coupled with a septum disposed within the septal aperture; having a thickness tapering in the radial direction; being made of mesh material with a plurality of wires between 0.004-0.008 inches (0.01016-0.02032 centimeters) in diameter; defining a delivery configuration in which the first fixation member and the second fixation member are collapsed along the longitudinal axis; and defining an anchoring configuration in which the first fixation member and the second fixation member define a septal aperture therebetween.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

Figure 1:
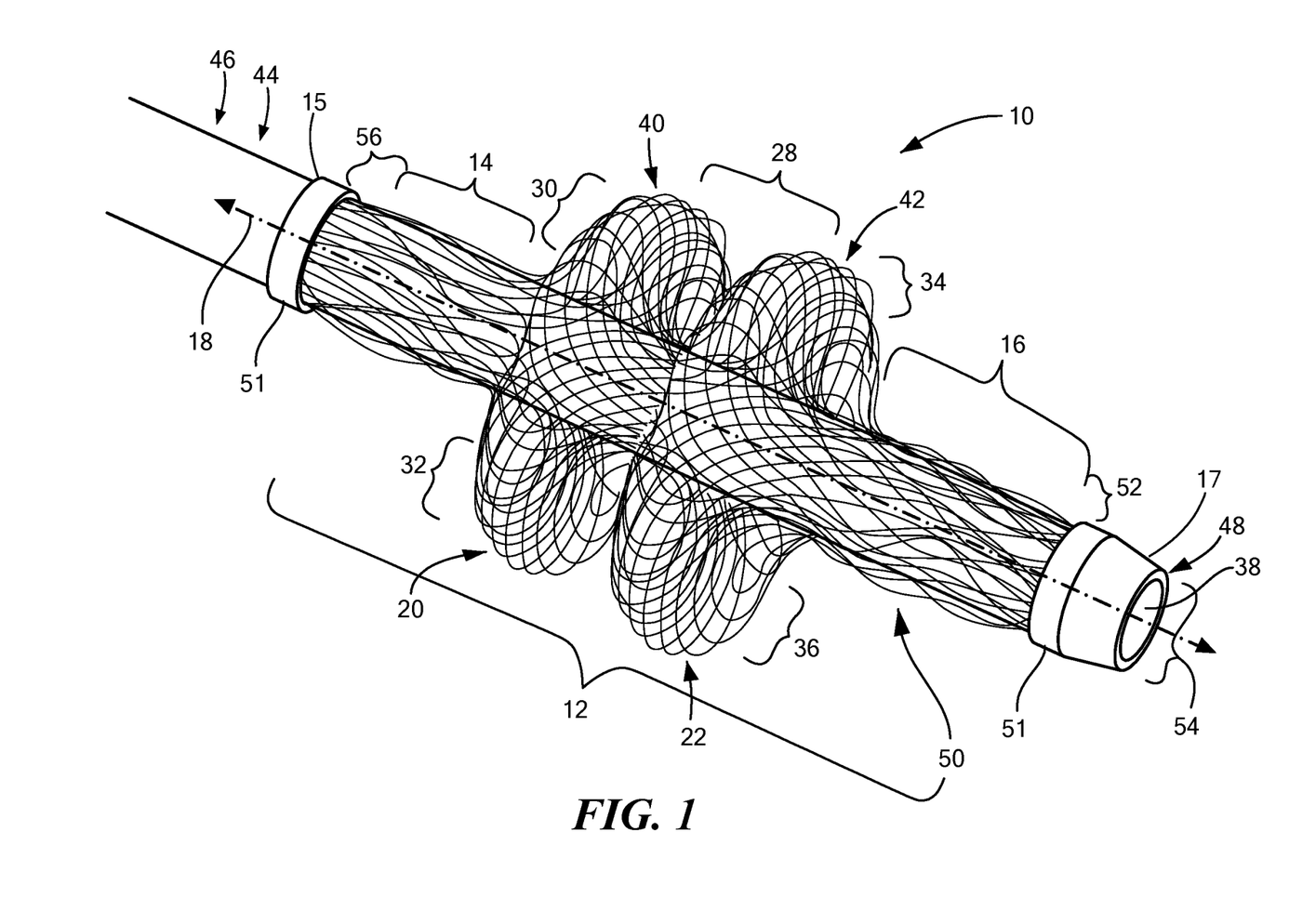
FIGS. 1 and 2 are perspective views of a medical fixation device constructed in accordance with an embodiment of the present invention.
Figure 2:
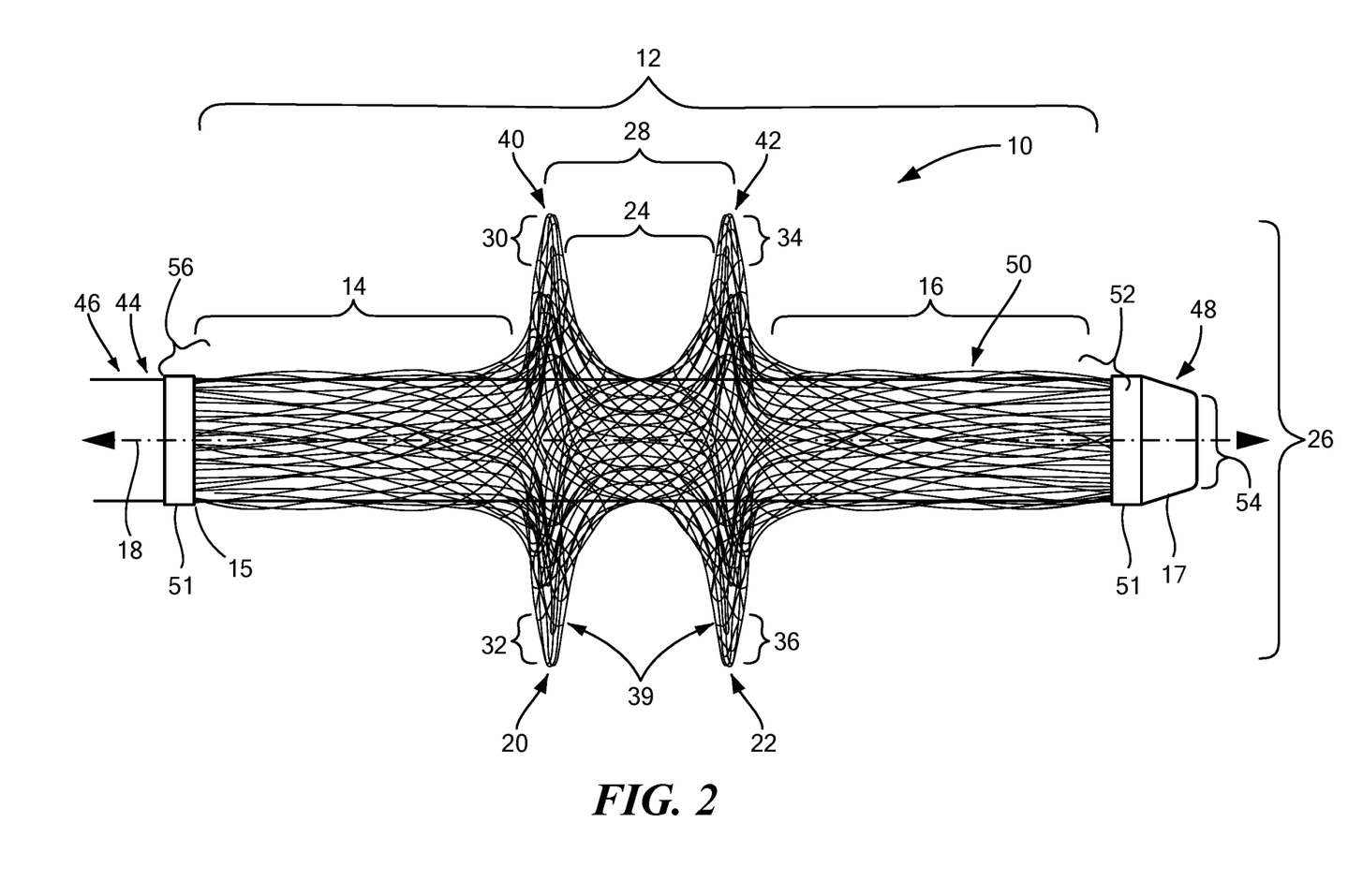

Now referring to the drawings in which like reference designators refer to like elements, there is shown in FIGS. 1-2 a medical fixation device constructed according to one embodiment of the invention and designated generally as "10." The medical fixation device 10 may be created using a mandrel and heat to cut a particular size and shape of the medical fixation device 10. The medical fixation device 10 may be customized in size and shape depending upon where and how the medical fixation device 10 is being used. Alternatively, different molds may be created such that the medical fixation device 10 may be created in different sizes and shapes depending upon which mold is being used. The medical fixation device 10 may be used with a mechanical circulating device such as an artificial heart, a ventricular assist device, or other device within the heart to provide support for the mechanical circulating device. The medical fixation device 10 may be implanted within the heart of a patient for any period of time and may be made out of a variety of different materials that are safe to be used inside the body for short or long periods of time. As a non-limiting example, these materials may include metal such as nickel titanium alloy as well as non-metal materials including polyethylene terephthalate, silicone, and membrane coating. The medical fixation device 10 may be composed entirely or in part of any of these materials and the design and orientation of the material/materials may depend upon which material/materials are being used. For example, the material may be a braided/mesh material or a solid material. As shown in FIGS. 1 and 2, a portion of the medical fixation device 10 may have a braided material and a portion of the medical fixation device 10 may be a solid material. In an alternative embodiment, the entire medical fixation device 10 may be made out of a braided material or the entire medical fixation device 10 may be made out of a solid material.

The medical fixation device 10 may include an elongate body 12 having a proximal portion 14 and a distal portion 16. The elongate body 12 may be made out of a mesh material that is flexible and/or may be a metal or non-metal material. Super-elastic wires may be used in the mesh and the wires may be made out of metals including a nickel-titanium alloy. Additional and/or alternative metals may be used including, but not limited to, stainless steel or cobalt chrome. The mesh may be made out of one wire or more than one wire and the diameter of the wires may all be the same or may be different sizes. The size of the mesh may also be variable and measured based upon the number of openings in the mesh e.g. a 4-mesh screen means there are four openings across one linear inch of screen. The size of the mesh may depend upon how much flexibility is desired in the elongate body 12 and can variable throughout the elongate body 12 or can be the same size throughout the elongate body 12. Alternatively, the elongate body 12 may be made out of a solid material such as a metal or plastic or it may be made out of a dissolvable material that may dissolve over a short or long period of time. Once the medical fixation device 10 is in place, a portion of the medical fixation device 10 or the entire medical fixation device 10 may dissolve.

A longitudinal axis 18 may extend though the elongate body 12 from the proximal portion 14 to the distal portion 16. The proximal portion 14 may be larger, smaller, or the same size as the distal portion 16 of the elongate body 12, depending upon the anatomical structure of the anatomy that the medical fixation device 10 is sized to be implanted within. The proximal portion 14 may have a proximal end 15 which is the furthest proximal part of the elongate body 12 and the distal portion 16 may have a distal end 17 which is the furthest distal part of the elongate body 12. The proximal end 15 and the distal end 17 may be made out of a braided mesh material or alternatively may be made out of a solid material. For example, if the elongate body 12 is made from a mesh material, the wire(s) may terminate at or near the proximal end 15 and/or the distal end 17 and therefore form a rough end. Alternatively, the wire(s) may be trimmed or bent in such a way as to form a smooth end. For example, a cap or other solid material may be used at the proximal end 15 and/or the distal end 17 or the entire elongate body 12 may be made from a solid material so that these ends are smooth such that the medical fixation device 10 can be safely implanted within the heart or another anatomical structure without damaging the heart or other tissue.

A first fixation member 20 may be disposed on the proximal portion 14 of the elongate body 12 configured to be implanted on at least one side of the septum of the heart or alternatively in another anatomical structure. A second fixation member 22 may be disposed on the distal portion 16 and spaced a distance away from the first fixation member 20 of the elongate body 12, be diametrically opposed to the first fixation member 20, and configured to be implanted on at least one side of the septum of the heart or alternatively in another anatomical structure. In an alternative configuration, the first fixation member 20 may be disposed on the proximal end 15 and the second fixation member 22 may be disposed on the distal end 17. The first fixation member 20 and the second fixation member 22 may be disposed anywhere along the elongate body 12. The first fixation member 20 may be disposed anywhere on the proximal portion 14 of the elongate body 12 and the second fixation member 22 may be disposed anywhere on the distal portion 16 of the elongate body 12. The second fixation member 22 may cooperate with the first fixation member 20 to define a septal aperture 24 therebetween. In a non-limiting example, the first fixation member 20 and the second fixation member 22 may be spaced a distance of between 1-3 millimeters ("mm") apart. The septal aperture 24 may be a variety of different sizes to accommodate different sized septums or any other sized anatomical structure. In alternative embodiments, there may be one fixation member or more than two fixation members as well.

Figure 7:
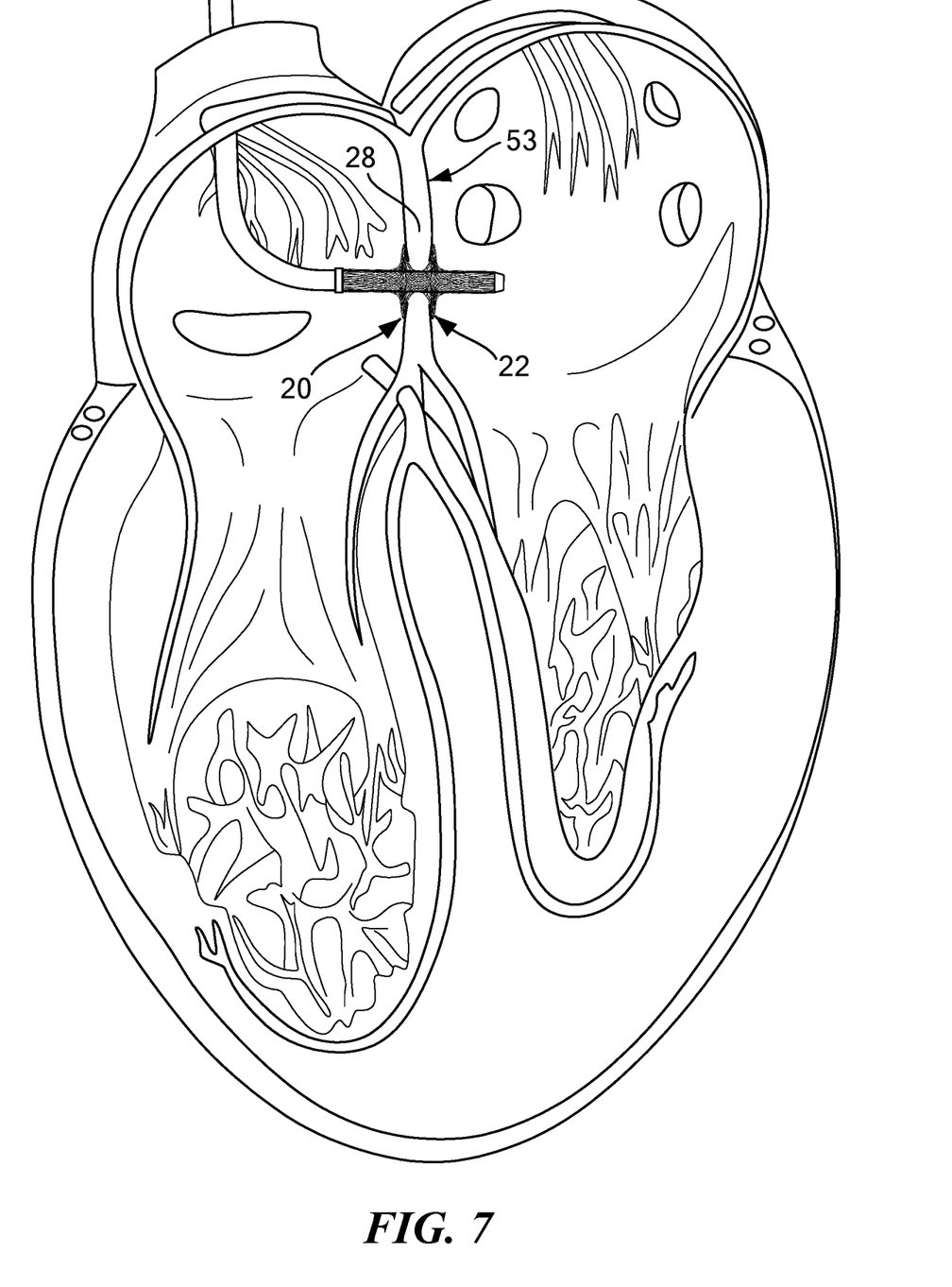
FIG. 7 is a view of the medical fixation device shown in FIG. 1 implanted within the septum of the heart.

The first fixation member 20 and the second fixation member 22 may be made out of a wire mesh, a solid material such as a plastic, a dissolvable material, or any other material that is safe to be used within the heart or another part of the body. The first fixation member 20 and the second fixation member 22 may be made out of the same material or different materials. Also, a portion of at least one of the first fixation member 20 and the second fixation member 22 may be made out of one material while another portion of the first fixation member 20 and/or the second fixation member 22 may be made out of a different material. If the material used for the first fixation member 20 and/or the second fixation member 22 is mesh, it may be made up of one wire or more than one wire and the diameter of the wires may be different or all the same. The size of the mesh may also be variable and measured based upon the number of openings in the mesh e.g. a 4-mesh screen means there are four openings across one linear inch of screen. The size of the mesh may be variable in different portions of the first fixation member 20 and/or the second fixation member 22 which may impact the flexibility of the material. When the medical fixation device 10 is implanted within the beating heart, the material may move with the heart and not cause damage to the tissue. The medical fixation device 10 may be placed in another anatomical structure or tissue and not damage the structure or tissue as well. In one configuration, the first fixation member 20 may be implanted on one side of the septum of the heart and the second fixation member 22 may be implanted on the other side of the septum of the heart (as shown in FIG. 7). Different embodiments of the medical fixation device 10 may have only one fixation member or more than two fixation members as well.

Figure 4:
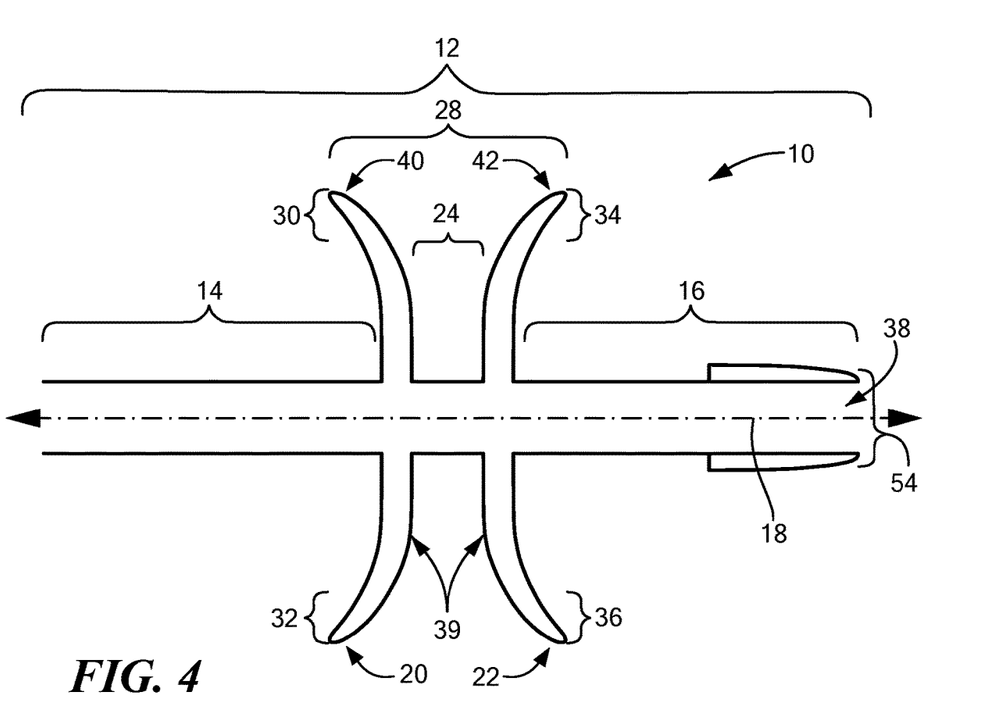
FIG. 4 is a perspective view of another medical fixation device constructed in accordance with an embodiment of the present invention.
Figure 5:
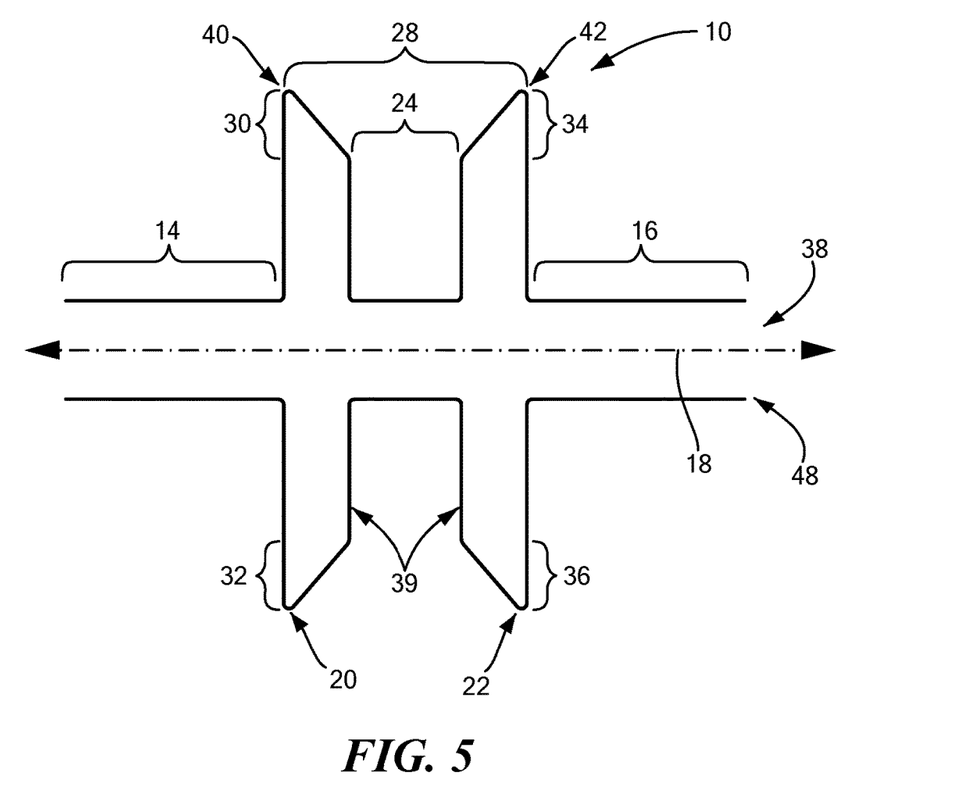
FIG. 5 is a perspective view of another medical fixation device in accordance with an embodiment of the present invention.
Figure 6:
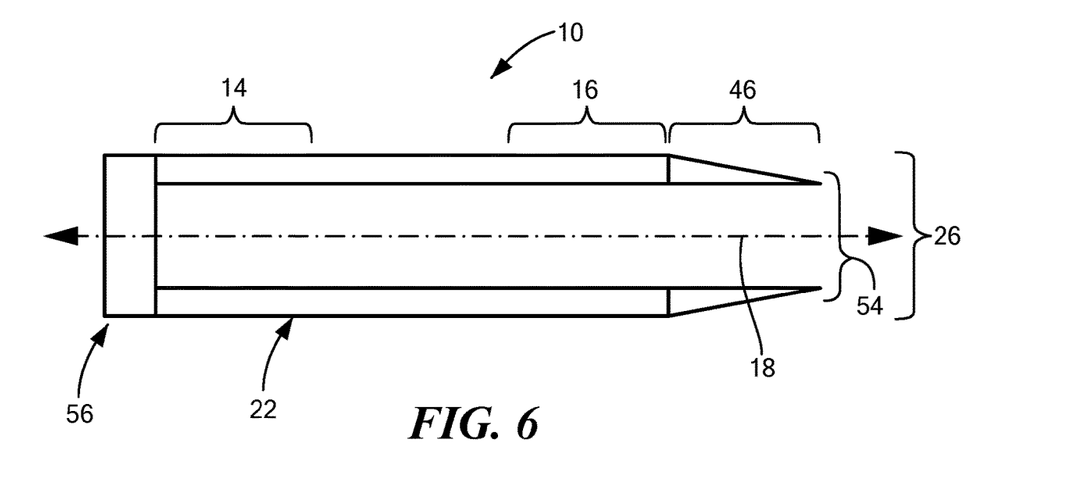
FIG. 6 is a perspective view of the medical fixation device shown in FIG. 5 in the delivery configuration.

The first fixation member 20 and the second fixation member 22 may be disposed in different configurations including a delivery configuration 26 (as shown in FIG. 6) and an anchoring configuration 28 (as shown in FIGS. 1, 2, 4 and 5). In the anchoring configuration 28, the first fixation member 20 and the second fixation member 22 may each extend radially outward from the elongate body 12. Since the first fixation member 20 and the second fixation member 22 may move from the delivery configuration 26 to the anchoring configuration 28, the first fixation member 20 and the second fixation member 22 may be movable to any position from being collapsed along the longitudinal axis 18 though the elongate body 12 to being perpendicular to the longitudinal axis 18 though the elongate body 12. The first fixation member 20 and the second fixation member 22 may be positioned in any other configuration between being collapsed to being perpendicular depending upon the particular anatomical structure that the medical fixation device 10 is being implanted within. The positioning of the first fixation member 20 may be different from the second fixation member 22 or may be the same. When the first fixation member 20 and the second fixation member 22 are in a desired position, the first fixation member 20 and the second fixation member 22 may be secured in place with, for example, a securing or locking mechanism to maintain the position of the first fixation member 20 and the second fixation member 22 as well as any other portion of the medical fixation device 10. The locking or securing mechanism may be used on one fixation member or both the first fixation member 20 and the second fixation member 22. In an alternative embodiment, the first fixation member 20 and the second fixation member 22 may be freely movable from any position and not securable.

In one embodiment, the first fixation member 20 may have a first tip 30 and a second tip 32 and the second fixation member 22 may have a third tip 34 and a fourth tip 36. The tips may all have the same shape, each have a different shape, or some may have the same shape while other tips may have a different shape. The tips may be shaped at an angle, be shaped like a mountain peak, an almond, an oval, flared, rounded, square, an arrow head, jagged, have an irregular shape, or any other desired shape. The tips may be in a variety of different positions and angles depending upon the particular anatomy of the heart or other anatomical structure, which shape is used for a particular tip, and how the medical fixation device 10 is to be implanted within, proximate to, or a distance from an anatomical structure. As a non-limiting example, the first tip 30 and the second tip 32 may face away from the third tip 34 and the fourth tip 36. See FIGS. 4 and 5. Alternatively, the first tip 30 and the second tip 32 may be parallel to the third tip 34 and the fourth tip 36. In other embodiments, the first tip 30 and the third tip 34 may face in the same direction, opposite directions, or be parallel to one another and the second tip 32 and the fourth tip 36 may face in the same direction, opposite directions, or be parallel to one another. In an alternative embodiment, the first fixation member 20 and the second fixation member 22 may extend transversely with respect to the elongate body 12 in the anchoring configuration 28 and the first tip 30 and the third tip 34 define a proximal most end and a distal most end of the first fixation member 20 and the first tip 40 and the third tip 42 define a proximal most end and a distal most end of the second fixation member 22.

The lengths and widths of the first fixation member 20 and the second fixation member 22 may be variable depending upon particular anatomy and may be sized differently to accommodate particular anatomical structures, particularly the septum of the heart. For example, the septal aperture 24 between the first fixation member 20 and the second fixation member 22 on the medical fixation device 10 may be between one to three millimeters in length. Accordingly, distance between the first fixation member 20 and the second fixation member 22 would correspond to the length of a particular anatomical structure. If the medical fixation device 10 is placed in the septum of the heart and the septal aperture 24 is placed in a hole in the septum, at least the first tip 30, the second tip 32, the third tip 34, and the fourth tip 36 of the first fixation member 20 and the second fixation member 22 would extend beyond the length and width of any hole in the septum when the medical fixation device 10 is at least in the anchoring configuration 28. As a non-limiting example, the length of the first fixation member 20 from the first tip 30 to the second tip 32 may be between 1.0-1.5 inches (2.54-3.81 centimeters) and the length of the second fixation member 22 from the third tip 34 to the fourth tip 36 may also be between 1.0-1.5 inches (2.54-3.81 centimeters). The length and width of the first fixation member 20 and the second fixation member 22 may be different or they may both be the same. The first fixation member 20 and the second fixation member 22 may be movable along the elongate body 12 such that they can be moved into different positions to accommodate different anatomical structures. For example, the first fixation member 20 and the second fixation member 22 may be spaced different distances apart along the elongate body such that the length of the septal aperture 24 may change. The first tip 30, the second tip 32, the third tip 34, and the fourth tip 36 may also be movable into different positions as well to accommodate different anatomical structures as well.

As seen in FIGS. 1 and 2, the first fixation member 20 and the second fixation member 22 may each have an interior surface 39 and the interior surface 39 of the first fixation member 20 and the interior surface 39 of the second fixation member 22 may face one another in a parallel orientation when the medical fixation device is in an anchoring configuration 28. When the medical fixation device 10 is in a delivery configuration 26, the interior surfaces 39 may be perpendicular to one another. In alternative configurations, at least a portion of the interior surfaces 9 may be perpendicular or parallel to one another depending upon how the first tip 30, the second tip 32, the third tip 34, and the fourth tip 36 are oriented.

The elongate body 12 of the medical fixation device 10 may define a channel 38 which runs along the longitudinal axis 18 of the elongate body 12 and the channel 38 may be sized to receive a cannula 44 therein. The size of the channel 38 may be variable depending upon the anatomy where it is to be used and the size of the cannula 44 to be received within the channel 38. For example, the channel 38 may be sized to receive a cannula 44 that has a diameter of 7 millimeters ("mm") and therefore the channel would have a diameter than is larger than 7 mm. As a non-limiting example, the channel 38 may be between 1-20 mm in diameter such that it can accommodate a variety of different sized cannulas 44 having different diameters as well as more than one cannula 44 at the same time. The channel 38 may have a variety of different diameters or may have the same diameter throughout. The size of the diameter of the channel 38 may be based upon certain vasculature as well as the anatomical structure where the medical fixation device 10 is being used. The cannula 44 may have a distal end 48 and a proximal end 46. The proximal end 46 of the cannula 44 may extend beyond the proximal end 15 of the proximal portion 14 of the elongate body 12 and the distal end 48 of the cannula 44 may extend beyond the end of the distal portion 16 of the elongate body 12. The proximal end 15 and the distal end 17 of the elongate body 12 may have a mechanism to secure or lock the elongate body 12 to/with the cannula 44 as well or the cannula 44 may not be secured or locked to/with the elongate body 12. In one embodiment, at least one from the group consisting of the group consisting of the first fixation member 20 and the second fixation member 22 may be disposed three to five millimeters from the distal end 48 of the cannula 44. The first fixation member 20 and the second fixation member 22 may be variable distances from the proximal end 15 of the proximal portion 14 of the elongate body 12, the end of the distal portion 16 of the elongate body 12, the proximal end 46 of the cannula 44, and the distal end 48 of the cannula 44.

Figure 3:
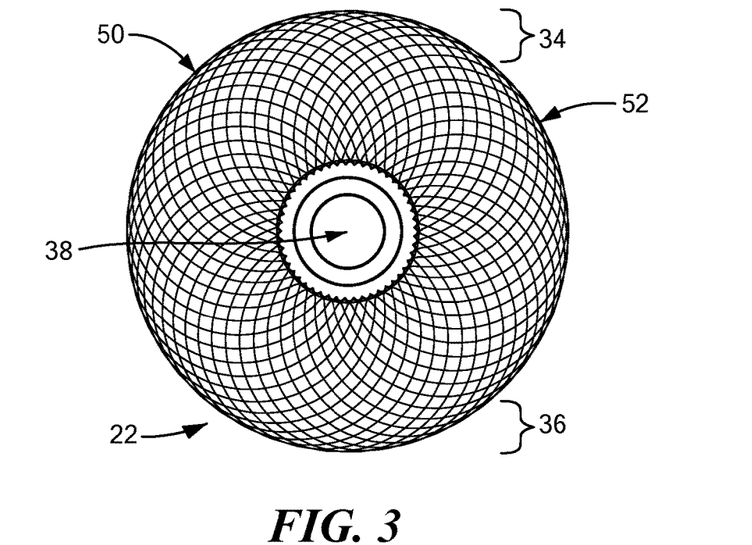
FIG. 3 is a side view of the medical fixation device shown in FIG. 1.

Now referring to FIG. 3, in one embodiment, at least one of the group consisting of the first fixation member 20, the second fixation member 22, and the elongate body 12 may be made from a mesh material 50. As shown in FIG. 3, at least one fixation member, which may include the first fixation member 20 and the second fixation member 22, may have the mesh material 50, may be comprised of a wire or a plurality of wires 52, and may also be flexible. Proximate the distal end 17 of the elongate body 12 there may be a connector 51 or other device and at least a portion of the first plurality of wires 52 may be disposed within at least a portion of the connector 51 or other device. The connector 51 may be in the shape of a ring or another shape may be used to create a smooth transition with the first plurality of wires 52 such that if the elongate body 12 is inserted into a patient's vasculature the first plurality of wires 56 will not injury or puncture the tissue. In an alternative embodiment, there may be a connector 51 or other device proximate the proximal end 15. Proximate the proximal end 15 of the elongate body 12 there may be a second plurality of wires 56. The second plurality of wires 56 may be at least partially disposed within the connector 51 or other device to create a smooth transition if the elongate body 12 is inserted into a patient's vasculature. In an alternative embodiment, the medical device 10 may not have a connector 51 or the medical fixation device 10 may only have one connector 51. This flexibility enables ease of movement of the first fixation member 20 and the second fixation member 22 into different positions, including transitioning between the anchoring configuration 28 and the delivery configuration 26 and also allows movement as the heart beats. Each wire 52 may have a diameter of between 0.004-0.008 inches (0.01016-0.02032 centimeters), but this size may be variable depending upon the anatomy that the medical fixation device 10 is being inserted and implanted into and the desired flexibility or rigidity of the first fixation member 20 and the second fixation member 22. In one embodiment, the plurality of wires 52 may include between thirty-six and seventy-two wires. The diameter of the first fixation member 20 and the second fixation member 22 may be the same. Alternatively, the first fixation member 20 may have a larger diameter than the second fixation member 22 or the first fixation member 20 may have a smaller diameter than the second fixation member 22. The diameter of the first fixation member 20 and the second fixation member 22 may be adjusted to correspond to a particular body part/anatomical structure. The length of the first fixation member 20 and the second fixation member 22 may be the same or alternatively, the first fixation member may be longer than the second fixation member 22 or the first fixation member 20 may be shorter than the second fixation member 22. The dimensions of the first fixation member 20 and the second fixation member 22 may be adjusted to correspond to a particular body part/anatomical structure. Also, the elongate body 12 may be made out of the mesh material 50 and the diameter of the elongate body 12 with the mesh material 50 may be between one and one and one-half inches (2.54-3.81 centimeters) in diameter. The mesh material 50 may be a woven, knit, or knotted material of open texture with evenly spaced holes or differently spaced holes. As can be seen in FIG. 3, the sizing of the holes in the mesh material 50 may be different in different portions of the first fixation member 20 and/or the second fixation member 22. The diameter of the elongate body 12 may be consistent or it may be different and depend upon particular anatomy.

In the embodiment as shown in FIG. 4, the first fixation member 20 and the second fixation member 22 may have a thickness that tapers in a radial direction. Alternatively, the first fixation member 20 and the second fixation member 22 may have a thickness that increases in a radial direction. Additionally, the first fixation member 20 and the second fixation member 22 may have different thicknesses at different portions of the first fixation member 20 and the second fixation member 22 depending upon the anatomy of the heart or other anatomical structure that the medical fixation device 10 is to be implanted within or they may have the same thickness throughout. When the medical fixation device 10 is in the anchoring configuration 28, the first tip 30, the second tip, 32, the third tip 34, and the fourth tip 36 may all face outwardly and curve away from the septal tissue to prevent erosion of the tissue in the heart or other anatomical structure. The first tip 30, the second tip, 32, the third tip 34, and the fourth tip 36 may also be pointed or be blunted. In the anchoring configuration 28, the first tip 30, the second tip, 32, the third tip 34, and the fourth tip 36 may all face inwardly and curve toward the septal tissue such that each tip may adhere to the septal tissue to secure the medical fixation device 10 in place.

As can be seen in FIG. 5, the first fixation member 20 and the second fixation member 22 may all have the same thickness and then the first tip 30, the second tip, 32, the third tip 34, and the fourth tip 36 may all have chamfered edges. When the medical fixation device 10 is implanted into the heart or other anatomical structure and the first fixation member 20 is on one side of the septum 53 and the second fixation member 22 is on the other side of the septum 53, the first tip 30, the second tip, 32, the third tip 34, and the fourth tip 36 may and taper away from the septum 53 to prevent erosion.

As illustrated in FIG. 6, the delivery configuration 26 of the medical fixation device 10 may provide a shape that allows for insertion of the medical fixation device 10 into the septum 53 or other anatomical structure. In the delivery configuration 26, the first fixation member 20 and the second fixation member 22 may be collapsed. When the first fixation member 20 and the second fixation member 22 are collapsed they may be flush with the surface of the elongate body 12 to allow for easy insertion and removal of the medical fixation device 10 into the heart.

The distal end 48 of the cannula 44 may be permanently or releasably secured to the elongate body 12. The cannula 44 may be removed from the medical fixation device 10 such that the medical fixation deice may remain in place in the heart or other anatomical structure. For example, if the medical fixation device 10 is implanted within the septum 53 of the heart, the cannula 44 may be inserted and/or removed from the medical fixation device 10 while the medical fixation device 10 remains implanted within the septum 53 of the heart. The distal end 48 of the cannula 44 may also terminate in a tip of the cannula 54 which may be flat or pointed. For example, the tip of the cannula 54 may be pointed, beveled or in another orientation. The tip of the cannula 54 may also have at least one tine to help fixate the medical fixation device 10 in place. The proximal portion 14 of the elongate body 12 may also have a proximal end 15 of the elongate body 12 which may be sized and shaped to anchor the fixation device in the septum 53. For example, the proximal end 15 of the elongate body 12 may be of a length such that it is larger than the septal aperture 24.

In FIG. 7, the medical fixation device 10 is shown disposed within the septum 53 of the heart. The medical fixation device 10 may be used within the vascular system or another anatomical structure. As a non-limiting example, the medical fixation device 10 may enter the heart of a patient through the superior vena cava, the inferior vena cava or any other portion of the vascular system. The first fixation member 20 and the second fixation member 22 may extend in a radial direction from and surrounding the elongate body 12 when coupled with a septum 53. When the medical fixation device 10 is disposed within the septum 53, the first fixation member 20 and the second fixation member 22 may be on either side of the septum 53 and may seal the septal aperture 24. When the medical fixation device 10 is disposed within the septum 53, the medical fixation device 10 may be configured to maintain the cannula 44 in the septum 53 to allow and maintain blood flow into and out of the cannula 44.

As these and other variations and combinations of the features described above can be employed, the foregoing description should be taken by way of illustration rather than by limitation of the present invention. Additional features of the present invention are disclosed in the numbered paragraphs set forth below.

What is claimed is:

1. A medical fixation device comprising:
   a first elongate body defining a proximal end, a distal end, and defining a lumen extending therethrough;
      a second elongate body having a proximal portion, a distal portion, and defining a longitudinal axis extending therethrough, the second elongate body further including a channel, the first elongate body being disposed within the channel and permanently secured to the second elongate body;
      a first fixation member on the proximal portion of the second elongate body; and
      a second fixation member on the distal portion of the second elongate body,
   wherein the medical fixation device includes a delivery configuration in which the first fixation member and the second fixation member are collapsed along the longitudinal axis and an anchoring configuration in which the first fixation member and the second fixation member each extend radially outward from the second elongate body and define a septal aperture therebetween, and
   wherein the medical fixation device in the anchoring configuration disposed in a septum of a heart is configured to maintain the lumen of the first elongate body open and the first elongate body has a length such that the first elongate body extends outside of the heart.

2. The medical fixation device of claim 1, wherein the first fixation member and the second fixation member extend transversely with respect to the second elongate body in the anchoring configuration.

3. The medical fixation device of claim 2, wherein at least one from the group consisting of the first fixation member and the second fixation member is disposed three to five millimeters from the distal end of the first elongate body.

4. The medical fixation device of claim 1, wherein the septal aperture is between one to three millimeters in length.

5. The medical fixation device of claim 1, wherein the first fixation member and the second fixation member are made of a mesh material.

6. The medical fixation device of claim 5, wherein the mesh material is flexible.

7. The medical fixation device of claim 6, wherein the mesh material includes a plurality of wires having a diameter between 0.004-0.008 inches (0.01016-0.02032 centimeters).

8. The medical fixation device of claim 1, wherein in the anchoring configuration, the first fixation member and the second fixation member each have an interior surface facing each other in a parallel orientation.

9. The medical fixation device of claim 1, wherein:
   the first fixation member includes a first tip and a second tip opposite the first tip, the first tip having a first edge and the second tip having a second edge;
   the second fixation member includes a third tip and a fourth tip opposite the third tip, the third tip having a third edge and the fourth tip having a fourth edge, the first tip being convex with respect to the third tip, the third tip being convex with respect to the first tip, the second tip being convex with respect to the fourth tip, and the fourth tip being convex with respect to the second tip; and
   the first fixation member and the second fixation member having a thickness tapering in the radial direction.

10. The medical fixation device of claim 5, wherein the mesh material is braided.

11. The medical fixation device of claim 10, wherein the plurality of wires include between 36 to 72 wires.

12. The medical fixation device of claim 1, wherein the first elongate body terminates in a beveled tip.

13. The medical fixation device of claim 1, wherein medical fixation device is configured to be disposed in a septum such as to allow and maintain blood flow into and out of the first elongate body.

14. The medical device of claim 1, wherein the first elongate body is a cannula.

15. The medical device of claim 1, wherein the length of the first elongate body is such that with medical fixation device in the anchoring configuration disposed in the septum, the first elongate body extends to the superior vena cava or the inferior vena cava.

* * * * *